(12) United States Patent
Adar et al.

(10) Patent No.: US 7,579,461 B2
(45) Date of Patent: Aug. 25, 2009

(54) PROCESSES FOR THE PREPARATION OF ROCURONIUM BROMIDE AND INTERMEDIATES THEREOF

(75) Inventors: Eliezer Adar, Omer (IL); David Sondack, Arad (IL); Oded Friedman, Talmey Yechiel (IL); Iosef Manascu, Omer (IL); Tamir Fizitzki, Beer-Sheva (IL); Boris Freger, Beer Sheva (IL); Oded Arad, Rechovot (IL); Alexander Weisman, Kiryat-Ekron (IL); Joseph Kaspi, Givatayim (IL)

(73) Assignee: Chemagis Ltd., Bnei Brak (IL)

( * ) Notice: Subject to any disclaimer, the term of this patent is extended or adjusted under 35 U.S.C. 154(b) by 959 days.

(21) Appl. No.: 11/034,510

(22) Filed: Jan. 13, 2005

(65) Prior Publication Data

US 2005/0159398 A1 Jul. 21, 2005

Related U.S. Application Data

(60) Provisional application No. 60/536,524, filed on Jan. 15, 2004.

(51) Int. Cl.
*C07J 43/00* (2006.01)
(52) U.S. Cl. .................................... 540/96
(58) Field of Classification Search ............... 540/96
See application file for complete search history.

(56) References Cited

U.S. PATENT DOCUMENTS 5,817,803 A 10/1998 Magni et al.

FOREIGN PATENT DOCUMENTS

| EP | 0287150 | * 10/1988 |
| WO | WO 2005/068487 | 7/2005 |

OTHER PUBLICATIONS

Slavikova et al., "Dihydrotestosterone with an ammonium centre in the position 16beta." Collect. Czech. Chem. Commun., vol. 62, pp. 656-664, 1997.*
Tuba et al. "Synthesis and Structure—Activity Relationship of Neuromuscular Blocking Agents", Current Medicinal Chemistry, 9(16): 1507-1536, 2002.

* cited by examiner

*Primary Examiner*—Barbara P Badio
(74) *Attorney, Agent, or Firm*—Leydig, Voit & Mayer, Ltd.

(57) ABSTRACT

A novel process for preparing (2β,3α,5α,16β,17β)-17-acetoxy-3-hydroxy-2-(4-morpholinyl)-16-(1-pyrrolidinyl) androstane, a known intermediate in the synthesis of the skeletal muscle relaxant rocuronium bromide, is disclosed.

28 Claims, No Drawings

PROCESSES FOR THE PREPARATION OF ROCURONIUM BROMIDE AND INTERMEDIATES THEREOF

This application claims the benefit of priority from U.S. Provisional Patent Application No. 60/536,524, filed Jan. 15, 2004, the teachings of which are incorporated herein in their entirety.

FIELD AND BACKGROUND OF THE INVENTION

The present invention relates to the field of chemistry and more particularly to a novel process of preparing (2β,3α,5α,16β,17β)-17-acetoxy-3-hydroxy-2-(4-morpholinyl)-16-(1-pyrrolidinyl)androstane, which is typically used as an intermediate in the preparation of rocuronium bromide.

Neuromuscular blocking agents (NMBA) are muscle-relaxing drugs having similar muscle paralyzing activity as the naturally occurring alkaloid d-tubocurarine, used for hunting for centuries by natives of South America who extract it from curare, a vine native to the Amazon Basin. These agents, used in modern clinical practice since 1942, are known to interrupt transmission of nerve impulses at the skeletal neuromuscular junction and cause skeletal muscle contraction to cease.

NMBAs are routinely used as anesthesia adjuvants in the operating theatre, to enable endotracheal intubation and to facilitate mechanical ventilation, i.e., relaxation of vocal cords, jaw muscles etc., to facilitate surgery, i.e., providing generalized muscle relaxation so as to allow surgical access to body cavities, in particular the abdomen and thorax, without hindrance from voluntary or reflex muscle movement, as relaxants to prevent the violent muscle movements associated with electroconvulsive therapy treatment, and for surgery under convulsive conditions. Typically, administration is performed intravenously by injection of a suitable dosage form.

Based on their mechanisms of action, NMBAs are divided into two categories: depolarizing and non-depolarizing.

Depolarizing neuromuscular blocking agents bind to nicotinic acetylcholine receptors (nAChRs) at the neuromuscular junction in a way similar to that of the endogenous neurotransmitter acetylcholine, but in a noncompetitive mode. They stimulate an initial opening of the ion channel, producing contractions known as fasciculations. However, since these drugs are cleared relatively slowly by cholinesterase enzymes, as compared to the very rapid hydrolysis of acetylcholine by acetylcholine esterases, they bind for a much longer period than acetylcholine, causing persistent depolarization of the end-plate and hence cause a neuromuscular block. Succinylcholine (Suxamethonium) is a classical example of a depolarizing NMBA.

Non-depolarizing neuromuscular blocking agents compete with acetylcholine for binding to muscle nAChRs, but unlike depolarizing NMBAs, they do not activate the channel. Rather, non-depolarizing NMBAs block the activation of the channel by acetylcholine and hence prevent cell membrane depolarization, and, as a result, the muscle becomes flaccid.

Most of the clinically-used NMBAs belong to the non-depolarizing category. These include tubocurarine, atracurium, (cis)atracurium, mivacurium, pancuronium, vecuronium, rapacuronium and rocuronium.

Hence, 1-[(2β,3α,5α,16β,17β)-17-acetoxy-3-hydroxy-2-(4-morpholinyl)-androstan-16-yl-]-1-(2-propenyl)pyrrolidinium bromide, also known by the name rocuronium bromide, is a neuromuscular blocking agent having a steroidal skeleton as shown hereinunder.

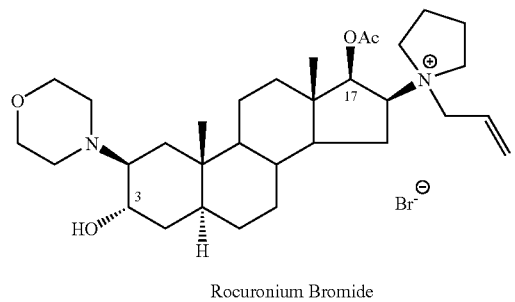

Rocuronium Bromide

Rocuronium bromide, which is presently marketed in the North America under the brand name ZEMURON® (rocuronium bromide) and elsewhere under the brand name ESMERON® (rocuronium bromide), is used in clinical practice since 1994 as a non-depolarizing neuromuscular blocking agent. It is known for its remarkable rapid yet controllable onset, depending on dose and intermediate duration. Rocuronium bromide is indicated for patients as an adjunct to general anesthesia, to facilitate both rapid sequence and routine tracheal intubation, and to provide skeletal muscle relaxation during surgery or mechanical ventilation.

Processes for preparing rocuronium bromide are described in U.S. Pat. Nos. 4,894,369 and 5,817,803, and in Tuba, Z. et al. (2002), "Synthesis and structure-activity relationships of neuromuscular blocking agents." *Curr. Med. Chem.* 9(16): 1507-36, which are all incorporated by reference as if fully set forth herein.

U.S. Pat. No. 5,817,803 describes a process of preparing rocuronium bromide, which involves acetylation of (2α,3α,5α,16β,17β)-2,3-epoxy-17-hydroxy-16-(1-pyrrolidinyl)androstane (Compound A, Scheme 1 below), so as to obtain Compound B (Scheme 1), and reacting Compound B with morpholine to yield a compound having the Formula I below, which is also referred to herein throughout as Compound I, as illustrated in Scheme 1 below. As is further detailed hereinbelow, Compound I is a known intermediate in the synthesis of rocuronium bromide.

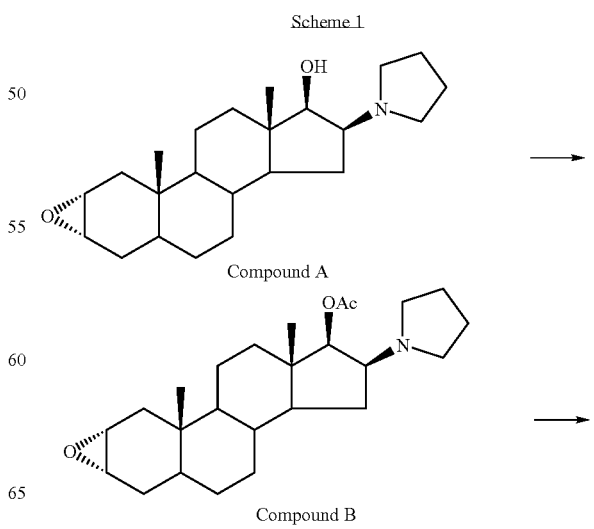

Scheme 1

Compound A

Compound B

-continued

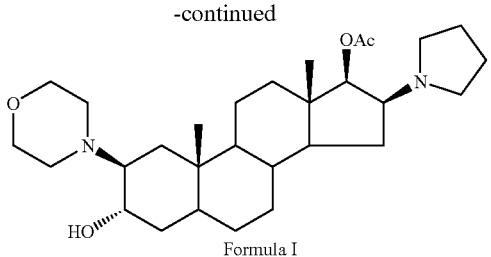

Formula I

U.S. Pat. No. 5,817,803 fails to provide any experimental data and therefore the efficiency of the process described therein, in terms of, for example, chemical yield and purity, is not demonstrated. A skilled artisan, however, can assume that reacting Compound B with morpholine, under the conditions described in this patent, may result in a side product formed between the morpholino and the acetoxy group at position 17 and therefore affect the efficiency of the process.

U.S. Pat. No. 4,894,369 teaches a process of preparing rocuronium bromide, in which the two final steps include a selective acetylation of (2β,3α,5α,16β,17β)-2-(4-morpholinyl)-16-(1-pyrrolidinyl)androstan-3,17-diol (a compound having Formula II below, which is also referred to herein throughout as Compound II) at position 17 to give (2β,3α,5α,16β,17β)-17-acetoxy-3-hydroxy-2-(4-morpholinyl)-16-(1-pyrrolidinyl)androstane (Compound I), followed by the allylation of the nitrogen on the pyrrolidine ring with allyl bromide, to thereby provide rocuronium bromide.

Formula II

Formula I

Such a selective acetylation at position 17, in which the hydroxyl at position 3 is left intact, is not a simple reaction to perform and hence adversely affects the process efficiency in terms of yield and product purification.

Indeed, the teachings of U.S. Pat. No. 4,894,369 demonstrate that the conversion of Compound II to. Compound I is inefficient. The crude product, Compound I, is obtained by treating Compound II with 1.13 equivalents of acetyl chloride in dichloromethane at room temperature for 18 hours, and purifying the crude product by column chromatography to give the desired Compound I at a yield of 48%. Therefore, this conversion technique reduce the overall efficiency of the process substantially and is further limited by the need to purify the product by column chromatography, which is known as a very inconvenient, expensive and time consuming procedure, especially in commercial scale.

U.S. Pat. No. 4,894,369 further teaches that performing the procedure described above in the presence of a 6.3 molar excess of acetyl chloride, results in the corresponding 3,17-diacetate(2β,3α,5α,16β,17β)-3,17-diacetoxy-2-(4-morpholinyl)-16-(1-pyrrolidinyl)androstane (a compound having Formula III below, which is also referred to herein throughout as Compound III). According to the teachings of this patent, Compound III is thus obtained as an off-white froth at 67% yield, while no additional purification of this compound was reported.

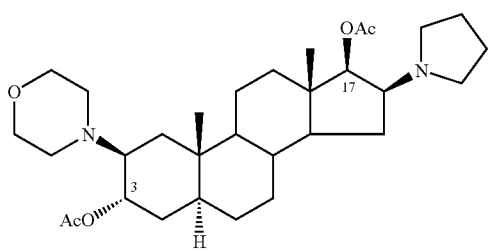

Formula III

Formula IV

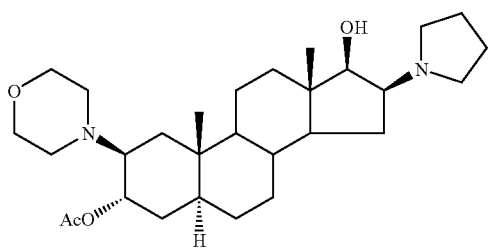

Reacting Compound III with methanol showed an undesired selectivity, according to U.S. Pat. No. 4,894,369, yielding as the main product (2β,3α,5α,16β,17β)-3-acetoxy-17-hydroxy-2-(4-morpholinyl)-16-(1-pyrrolidinyl) androstane (a compound having Formula IV above, which is also referred to herein throughout as Compound IV). Thus, the acetoxy group at position 3 is retained while the acetoxy group at position 17 is transformed to a hydroxyl group.

The greater susceptibility of the acetoxy group at position 17 to hydrolysis, as compared with the acetoxy group at position 3, is further supported in "Proceedings of the 4th Symposium on the Analysis of Steroids, Peos, Hungary, 1990, pp. 261-268". This article describes studies performed on a controlled hydrolysis of the two acetoxy groups (at the 3 and 17 positions) of vecuronium bromide (NORCURON® (vecuronium bromide)), a structurally related compound which is also used as a non-depolarizing neuromuscular blocking agent, as is illustrated below.

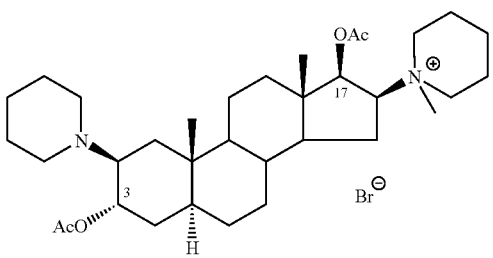

Vecuronium Bromide

According to the teachings of this reference, treating vecuronium bromide with methanol and sodium hydroxide yielded a mixture of the 3,17-dihydroxy corresponding compound and the 3-acetoxy-17-hydroxy corresponding compound. Under less drastic conditions, reacting vecuronium bromide with methanol gave the 3-acetoxy-17-hydroxy compound as a single product. These results, which indicate that under convenient hydrolytic conditions, the 3-acetoxy group is stable while the 17-acetoxy group is easily hydrolyzed, are in accord with the teachings of U.S. Pat. No. 4,894,369 cited above.

The above-cited article further teaches that under intense UV irradiation of a methanolic solution of vecuronium bromide, the selectivity is reversed such that the 17-acetoxy group is retained and the 3-acetoxy group is hydrolyzed. However, a process utilizing intense UV irradiation is highly impractical on a commercial scale.

There is thus a widely recognized need for, and it would be highly advantageous to have, an improved process for to the preparation of Compound I, devoid of the above limitations.

SUMMARY OF THE INVENTION

The present invention is of a novel, efficient and cost-effective process for the preparation of (2β,3α,5α,16β,17β)-17-acetoxy-3-hydroxy-2-(4-morpholinyl)-16-(1-pyrrolidinyl)androstane, a known intermediate in the synthesis of the neuromuscular blocking agent rocuronium bromide, and is therefore further of a novel process for the preparation of rocuronium bromide. The processes according to the present invention are based on the surprising findings that a selective de-acetylation of the respective diacetylated compound of (2β,3α,5α,16β,17β)-17-acetoxy-3-hydroxy-2-(4-morpholinyl)-16-(1-pyrrolidinyl)androstane can be performed in an acidic aqueous solution.

Thus, according to one aspect of the present invention, there is provided a process of preparing a compound having Formula I below.

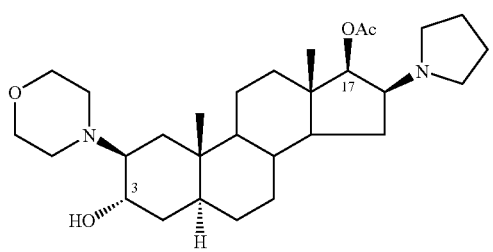

Formula I

The process, according to this aspect of the present invention comprises: providing a compound having Formula II:

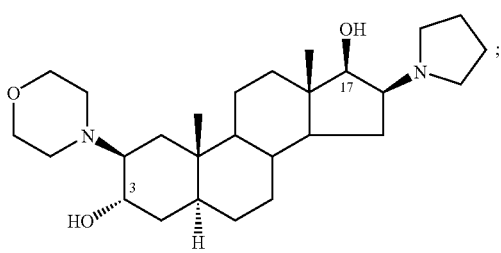

Formula II reacting the compound having Formula II with a molar excess of an acetylating agent, to thereby obtain a reaction mixture including a compound having Formula III:

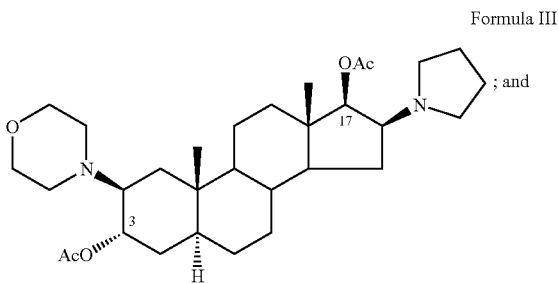

Formula III

; and contacting the reaction mixture with an aqueous solution of an acid, to thereby selectively deacetylate an acetoxy group at position 3 of the compound having Formula III.

According to further features in preferred embodiments of the invention described below, the acetylating agent is an acetyl halide, preferably acetyl chloride.

According to still further features in the described preferred embodiments the acetylating agent is acetic anhydride.

According to still further features in the described preferred embodiments the molar excess of the acetylating agent ranges from about 1.1 molar equivalents to about 5 molar equivalents, preferably from about 1.3 molar equivalents to about 1.7 molar equivalents, and more preferably is about 1.35 molar equivalents per one mol of the compound having the formula II.

According to still further features in the described preferred embodiments reacting the compound having the Formula II with an acetylating agent is performed at a temperature that ranges from room temperature to a temperature of about 90° C.

According to still further features in the described preferred embodiments the reacting is performed during a time period that ranges from 1 hour to 24 hours, preferably from 0.5 hour to 5 hours.

According to still further features in the described preferred embodiments reacting the compound having the Formula II with an acetylating agent is performed in the presence of an organic solvent, such as, but not limited to, dichloromethane and acetonitrile.

According to still further features in the described preferred embodiments the acid can be an organic acid such as, but not limited to, formic acid and a carboxylic acid, or an inorganic acid such as, but not limited to, hydrochloric acid, hydrobromic acid, hydriodic acid, sulfuric acid and phosphoric acid.

According to still further features in the described preferred embodiments contacting the reaction mixture with the aqueous solution of the acid is performed at a reflux temperature of the organic solvent and for a time period that ranges from 1 hour to 5 hours.

According to still further features in the described preferred embodiments the process further comprises purifying the compound having Formula I.

According to still further features in the described preferred embodiments the purification comprises recrystallizing the compound having Formula I.

According to yet another aspect of the present invention there is provided a compound having the Formula I described above, prepared by the process of the present invention, as described herein.

According to still further features in the described preferred embodiments the compound having Formula I has a purity of at least 85%, preferably of at least 90% and more preferably of at least 99%.

According to still another aspect of the present invention there is provided a process of preparing rocuronium bromide, which comprises:

providing a compound having the Formula I described above, according to the process described hereinabove; and reacting the compound having the Formula I with allyl bromide.

According to an additional aspect of the present invention there is provided rocuronium bromide prepared by the process described hereinabove The present invention successfully addresses the shortcomings of the presently known configurations by providing an improved process of preparing (2β,3α,5α,16β,17β)-17-acetoxy-3-hydroxy-2-(4-morpholinyl)-16-(1-pyrrolidinyl) androstane (Compound I, see formula I hereinabove), in terms of chemical yields, simplicity and purity of the product, which can be used in the preparation of rocuronium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used in this application, the singular form "a," "an," and "the" include plural references unless the context clearly dictates otherwise. For example, the term "a compound" includes a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein throughout, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Whenever a numerical range is indicated herein, it is meant to include any cited numeral (fractional or integral) within the indicated range. The phrases "ranging/ranges between" a first indicate number "and" a second indicate number and "ranging/ranges from" a first indicate number "to" a second indicate number are used herein interchangeably and are meant to include the first and second indicated numbers and all the fractional and integral numerals therebetween.

DESCRIPTION OF THE PREFERRED EMBODIMENTS

The present invention is of a novel process for the preparation of (2β,3α,5α,16β,17β)-17-acetoxy-3-hydroxy-2-(4-morpholinyl)-16-(1-pyrrolidinyl)androstane (Compound I, see Formula I hereinabove), a known intermediate in the synthesis of the skeletal muscle relaxant rocuronium bromide (1-[(2β,3α,5α,16β,17β)-17-acetoxy-3-hydroxy-2-(4-morpholinyl)androstan-16-yl]-1-(2-propenyl)pyrrolidinium bromide). The present invention is therefore further of a novel process of preparing rocuronium bromide, using the process of preparing Compound I. The present invention is further of highly pure 2β,3α,5α,16β,17β)-17-acetoxy-3-hydroxy-2-(4-morpholinyl)-16-(1-pyrrolidinyl)androstane and rocuronium bromide, prepared by these processes.

The principles and operation of the processes and the products thereof according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is described hereinabove, a typical process of preparing rocuronium bromide, as taught, for example, in U.S. Pat. No. 4,894,369, involves a conversion of Compound II (see, Formula II above) to Compound I (see, Formula I above), by selective acetylation of the hydroxy group at position 17. This conversion, which is performed by reacting Compound II with an acetylating agent (e.g., acetyl chloride), was found to be inefficient, resulting in relatively low yield and hence in a mixture of Compound I and Compound II. In order to purify the desired product of this conversion reaction, namely, Compound I, an inconvenient, time-consuming, cost-ineffective and environmentally-harmful purification process, in which column chromatography is typically utilized, should be performed. The inefficiency of this conversion reaction in terms of its simplicity, yield and purity of the desired product, renders the entire process of preparing rocuronium bromide inefficient.

In a search for an improved process of preparing the intermediate (2β,3α,5α,16β,17β)-17-acetoxy-3-hydroxy-2-(4-morpholinyl)-16-(1-pyrrolidinyl)androstane (Compound I, see Formula I hereinabove), and thus for an improved process of preparing rocuronium bromide, the present inventors have studied the selective acetylation reaction described above. As is demonstrated in the Examples section that follows (see, Reference Examples 1-5), the acetylation of Compound II was studied while performing the reaction under varying conditions and using two different acetylating agents (acetyl chloride and acetic anhydride). The results in these studies reestablished that although the OH (hydroxy) group at position 17 is more prone to acetylation, as compared with the hydroxy group at position 3, this alone is not enough for efficient production of Compound I, and therefore the latter is typically obtained in such an acetylation reaction either as a mixture contaminated with significant amounts of the starting material Compound II and optionally the di-acetylated product (2β,3α,5α,16β,17β)-3,17-diacetoxy-2-(4-morpholinyl)-16-(1-pyrrolidinyl)androstane (Compound III, see formula III hereinabove), and/or in low to moderate chemical yields.

As is further discussed hereinabove, previous studies indicated that over acetylation of Compound II, using an excess of an acetylating agents, results in the 3,17-diacetylated Compound III (see, Formula III above). However, it was further indicated that deacetylation of Compound III resulted in undesired selectivity, namely, deacetylation of the acetyl group at position 17. These findings are in accord with the enhanced reactivity of position 17, towards both acetylation and deacetylation reactions.

While continuing the search for an improved process for preparing rocuronium bromide, the present inventors have now surprisingly found that the 3,17-diacetylated Compound III, easily obtained by over acetylation of Compound II, when treated with an aqueous solution of an acid, readily and selectively transforms to the desired Compound I.

Based on these findings, the present inventors have designed and successfully performed a novel process of preparing Compound I, by reacting Compound II with a molar excess of an acetylating agent and selectively deacetylating the resulting product (Compound III) in an aqueous acidic environment. As is demonstrated in the Examples section that follows, using this process, Compound I was readily obtained in high yield and purity and was further easily purified using a simple and cost-effective recrystallization.

Hence, according to one aspect of the present invention, there is provided a process of preparing Compound I, which comprises:

providing Compound II;

reacting Compound II with a molar excess of an acetylating agent, to thereby obtain a reaction mixture including Compound III; and contacting the reaction mixture with an aqueous solution of an acid, to thereby selectively deacetylate an acetoxy group at position 3 of Compound III.

The starting material, Compound II, can be prepared according to procedures known in the art (see, for example, U.S. Pat. Nos. 4,894,369 and 5,817,803, and Tuba, Z. et al. (2002), *Curr. Med. Chem.* 9(16), 1507-36).

According to the process of the present invention, the starting material Compound II is subjected to an acetylation reaction which is performed by reacting it with a molar excess of an acetylating agent, as is detailed hereinunder.

The phrase "acetylating agent", as used herein, describes a chemical reagent which comprises an acetyl group, as defined herein, and is capable of reacting with a functional group, typically via a nucleophilic-addition reaction, so as to convert the functional group to an acetate group.

Representative examples of acetylating agents include, without limitation, acetyl halides and acetic anhydride.

As used herein, the term "acetyl halide" describes a $CH_3(C=O)X$ group wherein X is halide, as defined herein.

The term "halide" describes fluorine, chlorine, bromine or iodine.

The phrase "acetic anhydride" describes $CH_3(C=O)-O-(C=O)CH_3$.

According to a preferred embodiment of the present invention, the acetylating agent is an acetyl halide, preferably acetyl chloride.

The process according to the present invention calls for over-acetylation of the starting material, Compound II. This is achieved by using a molar excess of the acetylating agent.

As used herein, the phrase "molar excess" describes a molar amount of the acetylating agent that is greater than the molar amount of the substrate to be acetylated (herein, Compound II), such that the molar ratio between the acetylating agent and substrate is greater than 1:1.

Hence, according to a preferred embodiment of the present invention, the molar ratio between the acetylating agent and Compound II ranges from about 1.1 molar equivalents to about 5 molar equivalents per one mol of Compound II, preferably from about 1.3 to molar equivalents to about 1.7 molar equivalents per one mol of Compound II. An exemplary preferred molar ratio is about 1.35 molar equivalents per one mol of Compound II.

As used herein the term "about" refers to ±10%.

The reaction is typically performed in a solvent, which can be any anhydrous inert organic solvent and is preferably selected from those typically used for acetylation reactions, such as, but not limited to, acetone, acetonitrile, dichloroethane, dichloromethane, dimethylformamide, dimethylsulfoxide, dioxane, isopropanol, methanol, N,N-dimethylformamide and tetrahydrofurane. According to a preferred embodiment of the present invention, the organic solvent is dichloromethane or acetonitrile.

The reaction between Compound II and the acetylating agent can be performed at any temperature ranging from room temperature and a reflux temperature of the solvent, depending on the selected solvent, the selected acetylating agent and any other practical consideration. Thus, for example, using dichloromethane as the solvent, the acetylation reaction can be performed at room temperature or at about 30-40° C. Using acetonitrile as the solvent, the acetylation reaction can be performed at room temperature or at about 90° C. The reaction can also be performed at lower temperatures, although longer reaction times are expected to be dictated thereby.

Depending on the reaction conditions, the acetylation reaction according to the present invention is typically performed for a time period that ranges from about 1 hour to about 24 hours. At elevated (e.g., reflux) temperatures, the reaction time typically ranges between about 0.5 hour and about 5 hours.

Using a molar excess of the acetylating agent as described above, and suitable reaction conditions, the acetylation reaction of Compound II is shifted toward the production of the di-acetylated product, Compound III. Hence, the reaction mixture obtained by reacting Compound II and the acetylating agent includes, as a major component, Compound III.

As used herein, the phrase "reaction mixture" describes a mixture of products, solvents and reagents obtained upon ceasing the reaction.

Depending on the molar excess used in the acetylation reaction, the obtained reaction mixture can include, in addition to the diacetylated Compound III, the monoacetylated Compound I.

Since a typical molar excess according to preferred embodiments of the present invention is about 1.35, the reaction mixture typically includes a mixture of Compound III and Compound I.

A typical reaction mixture according to the present invention therefore includes from about 40% to about 60% of Compound III and from about 30% to about 70% of Compound I. As is demonstrated in the Examples section that follows, in a representative experiment (see, Example 1), a reaction mixture includes 55.5% of Compound III and 35.1% of Compound I.

As is further demonstrated in the Examples section that follows, such a reaction mixture, when subjected to selective deacetylation under acidic conditions, as is detailed hereinunder, results in substantial enrichment of Compound I while maintaining a high chemical yield thereof.

Thus, according to this process of the present invention, Compound III obtained in the acetylation reaction described above, is selectively hydrolyzed by contacting the reaction mixture described above with an aqueous solution of an acid. As mentioned hereinabove, the present inventors have surprisingly found that under these conditions, the susceptibility of the acetate group at position 3 to hydrolysis is substantially higher than that of the acetate group at position 17 and hence, Compound III is transformed to Compound I in high yields.

Contacting the reaction mixture with an aqueous solution of an acid is preferably performed at elevated temperatures and, more preferably, at a reflux temperature. Depending on the reaction conditions, the selective deacetylation reaction according to the present invention is typically performed for a time period that ranges from about 1 hour to about 24 hours. At elevated (e.g., reflux) temperatures, the reaction can be from about 0.5 hour to about 10 hours, more preferably from about 1 hour to about 5 hours.

The acid used in the selective deacetylation reaction can be an organic acid or an inorganic acid. Exemplary inorganic acids that are usable in this context of the present invention include, without limitation, hydrochloric acid, hydrobromic acid, hydroiodic acid, sulfuric acid and phosphoric acid.

Exemplary organic acids that are usable in this context of the present invention include, without limitation, formic acid and various carboxylic acids.

The phrase "carboxylic acid" as used in this context of the present invention, refers to RCOOH, where R can be alkyl, cycloalkyl or aryl.

According to a preferred embodiment of the present invention, the acid is hydrochloric acid (HCl), used at a concentration of from about 5% to 20%. An exemplary aqueous solution of an acid is 10% HCl.

By using a selective deacetylation as described hereinabove, the proportion of Compound I in the reaction mixture is substantially enriched. Thus, for example, in an exemplary experiment (see, Example 1 in the Examples section that follows), the ratio of Compound I to Compound III in the reaction mixture changes upon the acidic deacetylation from 0.63 to 9.80, a 15.5 fold enrichment factor. These results demonstrate the unexpected high liability of the 3-acetoxy group and the stability of the 17-acetoxy group under the reaction conditions used in the process of the present invention.

Once the selective deacetylation is completed, the desired product, Compound I, may be isolated from the reaction mixture by conventional work-up procedures known in the art. As is demonstrated in the Examples section that follows, Compound I is thus obtained in a chemical yield greater than 80% (e.g., 84%) and high purity of at least 90%, preferably at least 94%.

In an exemplary experiment, the desired Compound I was obtained in a chemical yield of about 84% and a purity, as determined by HPLC, of 94.1%. The respective ratio of Compound I/Compound II/Compound III in the process's product was 94.1/1.6/2.1.

Hence, using the process according to this aspect of the present invention, the starting material Compound II is almost completely converted to the desired Compound I and thus the major limitations associated with the presently known processes, namely, an inefficient reaction and the need to separate the reaction products by column chromatography, are circumvented.

Compound I can be further purified, so as to remove residual amounts of the diacetylated Compound III. Compound I and Compound III can be readily separated by simple batch purification methods such as recrystallization.

Hence, according to a preferred embodiment of this aspect of the present invention, the process described above can further comprise purifying the product, preferably by recrystallization. Suitable solvents for recrystallization include, without limitation, acetone, hexane, cyclohexane, heptane, acetonitrile and any combination thereof. As is demonstrated in the Examples section that follows (see, for example, Example 2) upon recrystallization from acetone, Compound I, having a purity greater that 99%, as determined by HPLC, is obtained. An even higher purity can be obtained following consecutive recrystallization processes of Compound I, e.g., recrystallization from acetone or acetonitrile, followed by additional recrystallization from acetonitrile. These results demonstrate the high efficiency and cost effectiveness of the process according to the present invention.

As discussed hereinabove, Compound I is typically used as an intermediate in the preparation of rocuronium bromide, a well-known and widely used non-depolarizing neuromuscular blocking agent. Using the process described above for preparing Compound I and thereafter converting Compound I to rocuronium bromide may therefore enhance the efficiency and cost effectiveness of the entire process of preparing rocuronium bromide.

Hence, according to another aspect of the present invention there is provided a process of preparing rocuronium bromide, which comprises preparing Compound I as described hereinabove and reacting Compound I with allyl bromide, so as to obtain rocuronium bromide.

Reacting Compound I with allyl bromide can be performed according to procedures known in the art (see, for example, U.S. Pat. Nos. 4,894,369 and 5,817,803, and Tuba, Z. et al. (2002), *Curr. Med. Chem.* 9(16), 1507-36).

Thus, the highly improved process for preparing Compound I according to the present invention provide a significant improvement for the process of preparing rocuronium bromide.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

(2β,3α,5α,16β,17β)-17-acetoxy-3-hydroxy-2-(4-morpholinyl)-16-(1-pyrrolidinyl)androstane is referred to hereinbelow as Compound I;

(2β,3α,5α,16β,17β)-2-(4-morpholinyl)-16-(1-pyrrolidinyl)androstane-3,17-diol is referred to hereinbelow as Compound II;

(2β,3α,5α,16β,17β)-3,17-diacetoxy-2-(4-morpholinyl)-16-(1-pyrrolidinyl)androstane is referred to hereinbelow as Compound III.

REFERENCE EXAMPLE 1

Acetyl chloride (1.92 ml, 0.027 mole) was added to a solution of (2β,3α,5α,16β,17β)-2-(4-morpholinyl)-16-(1-pyrrolidinyl)androstane-3,17-diol (Compound II, 10.7 grams, 0.024 mole) in 340 ml of dichloromethane. The reaction was set aside at room temperature (about 23° C.) for 18 hours. The pH was thereafter adjusted to 7.5 using 5% sodium bicarbonate solution. The aqueous phase was removed and the organic phase was washed with two portions of 50 ml of water, dried with $Na_2SO_4$, and the dichloromethane was evaporated to dryness to yield 7 grams of the crude residue as a crystalline mass.

HPLC analysis showed that the product included 67.2% of the desired Compound I, 7% of the starting material Compound II and 9.8% of the diacetate, Compound III.

REFERENCE EXAMPLE 2

The procedure of Example 1 was repeated at 40° C. The residue obtained, as determined by HPLC, was a mixture of 56.7% of the desired Compound I, 3.9% Compound II and 21.7% of Compound III.

REFERENCE EXAMPLE 3

The procedure of Example 1 was repeated at 0° C. The residue obtained, as determined by HPLC, was a mixture of 60.1% of the desired Compound I, 16.0% Compound II and 6.2% Compound III.

REFERENCE EXAMPLE 4

Acetic anhydride (2 ml, 0.02 mole) was added to a slurry of Compound II (5.3 grams, 0.01186 mole) in 100 ml of acetonitrile. The reaction mixture was refluxed for 1 hour. The solvent was evaporated to dryness to yield 6 grams of a solid residue. HPLC analysis showed that the residue contained 53.4% of the desired Compound I, 0.6% of Compound II and 39.5% of Compound III.

REFERENCE EXAMPLE 5

Acetic anhydride (1.3 ml, 0.013 mole) was added to a slurry of Compound II (5.3 grams, 0.01186 mole) in 100 ml of acetonitrile. The reaction mixture was refluxed for 1 hour. The reaction mixture was cooled and the residue was filtered on paper to yield 2.6 grams of solid mass. HPLC analysis showed that the product contains 96.1% of the desired Compound I, 0.4% of Compound II and 0.2% of Compound III.

EXAMPLE 1

Acetyl chloride (23.0 ml, 0.3234 mole) was added to a solution of Compound II (107 grams, 0.2395 mole) in 2 liters of dichloromethane. The reaction mixture was set-aside for 24 hours at room temperature (about 23° C.). HPLC analysis of a reaction sample showed that the mixture contained 35.1% of Compound I, 0.3% of Compound II and 55.5% of Compound III. Aqueous HCl solution (10.5%, 305 ml) was added thereafter and the mixture was heated to reflux for 4 hours. After cooling to 2° C., the mixture was neutralized to pH 7.2 by adding 5 liters of 5% sodium bicarbonate solution, and the aqueous phase was removed. HPLC analysis of the organic phase showed a composition of 86.3% of the desired Compound I, 1.9% of Compound II and 8.8% of Compound III.

The organic phase was washed with two portions of 500 ml of water, dried with $Na_2SO_4$ and the dichloromethane was removed by evaporation. The residue was obtained as yellow crystals (98.4 grams, 84% yield). HPLC analysis of the residue showed it contained 94.1% of the desired Compound I, 1.6% of Compound II and 2.1% of Compound III.

EXAMPLE 2

The product of the previous example was crystallized from acetone to give the desired Compound I in purity of 98.8%, as determined by HPLC, and in 45-55% chemical yield. The product contained residual amounts of Compound II (about 1.1%) and Compound III (about 0.062%), as determined by HPLC analysis. Similar results were obtained by crystallization from acetonitrile.

The recrystallized Compound I, obtained as described above, was subjected to a second recrystallization, from acetonitrile, to give Compound I in a chemical yield of 87% and purity of about 99.9%, as determined By HPLC. The product contained residual amounts of Compound II (about 0.09%), whereby Compound III was not detected.

EXAMPLE 3

A solution of Compound II (225 grams, 0.504 mole), acetyl chloride (55 grains, 0.728 mole) and dichloromethane (4.25 liters) was stirred for 4 hours at 35° C. 10% aqueous HCl was then added to the reaction mixture, the organic phase was separated and the aqueous phase was heated for 1 hour at 50° C. The resulting mixture was thereafter transferred to a holding vessel and was thereafter added gradually (during 5 minutes) to a stirred, cooled mixture of a 20% solution of $KHCO_3$ (707 grams in 3 liters) and dichloromethane (1.3 liters), while maintaining the temperature at 10° C. The resulting mixture was stirred for 20 minutes and the organic phase was thereafter separated and washed twice with 0.5 liter water. The solvent was then evaporated to give Compound I (160 grams, 0.328 mole) having a purity of about 95%, as determined by HPLC.

EXAMPLE 4

Allyl bromide (10 ml, 0.116 moles) was added to a solution of Compound I, prepared according to the Examples above (24.5 grams, 0.05 moles), in 250 ml of acetone. The solution was heated to reflux for 10 hours. The solvent was removed under reduced pressure to give 28 grams of rocuronium bromide having a purity of 98%, as determined by HPLC.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace, all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A process of preparing a compound having Formula I:

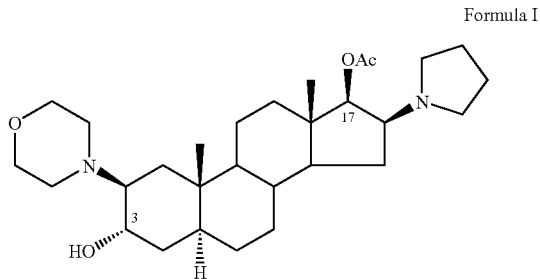

Formula I the process comprising:
reacting a compound having Formula II:

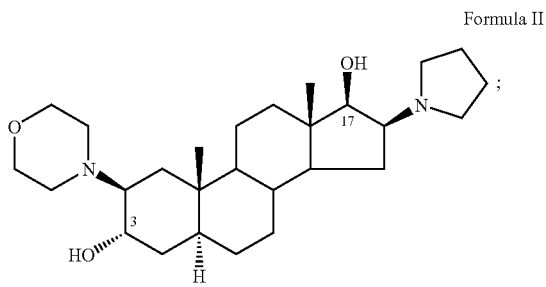

Formula II with a molar excess of an acetylating agent, to thereby obtain a reaction mixture including a compound having Formula III:

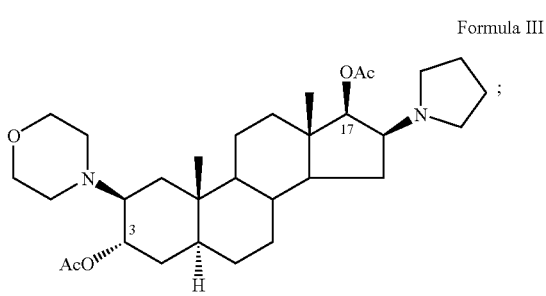

Formula III and
contacting said reaction mixture with an aqueous solution of an acid, to thereby selectively deacetylate an acetoxy group at position 3 of said compound having Formula III, thereby obtaining the compound having Formula I.

2. The process of claim 1, wherein said acetylating agent is selected from acetyl chloride and acetic anhydride.

3. The process of claim 1, wherein said molar excess of said acetylating agent ranges from about 1.1 molar equivalents to about 5 molar equivalents per one mol of said compound having said formula II.

4. The process of claim 3, wherein said molar excess of said acetylating agent is about 1.35 molar equivalents per one mol of said compound having said formula II.

5. The process of claim 1, wherein said reacting is performed in the presence of an organic solvent.

6. The process of claim 5, wherein said organic solvent is selected from dichloromethane and acetonitrile.

7. The process of claim 1, wherein said acid is selected from an organic acid and an inorganic acid.

8. The process of claim 7, wherein said acid is selected from hydrochloric acid, hydrobromic acid, hydriodic acid, sulfuric acid and phosphoric acid.

9. The process of claim 7, wherein said acid is selected from formic acid and a carboxylic acid.

10. The process of claim 5, wherein said contacting said reaction mixture with said aqueous solution of said acid is performed at a reflux temperature of said organic solvent.

11. The process of claim 1, further comprising purifying the compound having Formula I.

12. The process of claim 11, wherein said purifying comprises recrystallizing the compound having Formula I.

13. process of claim 1, wherein the compound of Formula I is obtained in a purity of at least 90 %.

14. The process of claim 12, wherein the compound of Formula I is obtained in a purity of at least 99 %.

15. A process of preparing rocuronium bromide, the process comprising:
reacting a compound having Formula II:

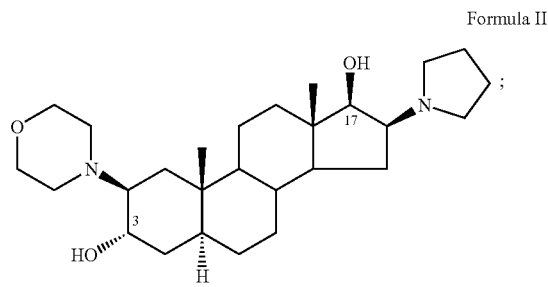

Formula II with a molar excess of an acetylating agent, to thereby obtain a reaction mixture including a compound having Formula III:

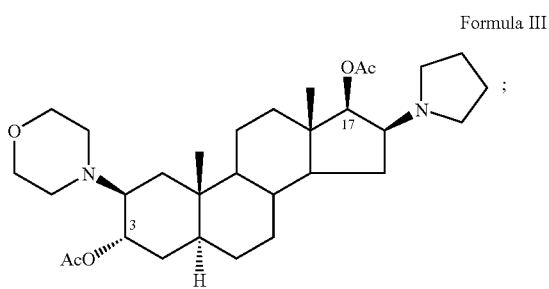

Formula III contacting said reaction mixture with an aqueous solution of an acid, to thereby selectively deacetylate an acetoxy group at position 3 of said compound having Formula III, to thereby provide a compound having Formula I

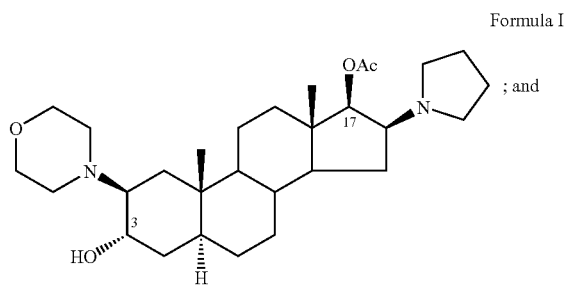

Formula I

; and reacting said compound having said Formula I with allyl bromide, thereby obtaining rocuronium bromide.

16. The process of claim 15, wherein said acetylating agent is selected from the group consisting of acetyl chloride and acetic anhydride.

17. The process of claim 15, wherein said molar excess of said acetylating agent ranges from about 1.1 molar equivalents to about 5 molar equivalents per one mol of said compound having said formula II.

18. The process of claim 17, wherein said molar excess of said acetylating agent is about 1.35 molar equivalents per one mol of said compound having said formula II.

19. The process of claim 15, wherein said reacting is performed in an organic solvent.

20. The process of claim 19, wherein said organic solvent is selected from the group consisting of dichloromethane and acetonitrile.

21. The process of claim 15, wherein said acid is selected from an organic acid and an inorganic acid.

22. The process of claim 21, wherein said acid is selected from the group consisting of hydrochloric acid, hydrobromic acid, hydriodic acid, sulfuric acid and phosphoric acid.

23. The process of claim 21, wherein said acid is selected from formic acid and a carboxylic acid.

24. The process of claim 19, wherein said contacting of said product with said aqueous solution of said acid is performed at a reflux temperature of said organic solvent.

25. The process of claim 1, further comprising purifying the compound having Formula I.

26. The process of claim 25, wherein said purifying comprises recrystallizing the compound having Formula I.

27. The process of claim 25, further comprising converting the compound of formula I into rocuronium bromide.

28. The process of claim 27, comprising reacting the compound of formula I with allyl bromide to produce the rocuronium bromide.

* * * * *